(12) United States Patent
Rieberer

(10) Patent No.: US 7,363,829 B2
(45) Date of Patent: Apr. 29, 2008

(54) DRILL CUTTING SAMPLER

(76) Inventor: Willy Rieberer, P.O. Box 1646, Cochrane, Alberta (CA) T4C 1B5

( * ) Notice: Subject to any disclaimer, the term of this patent is extended or adjusted under 35 U.S.C. 154(b) by 0 days.

(21) Appl. No.: 11/407,078

(22) Filed: Apr. 20, 2006

(65) Prior Publication Data

US 2007/0245838 A1    Oct. 25, 2007

(51) Int. Cl.
*G01N 1/04* (2006.01)

(52) U.S. Cl. ............... 73/863.23; 73/152.25; 73/152.04

(58) Field of Classification Search ........... 73/863.23, 73/152.04, 152.23, 152.25
See application file for complete search history.

(56) References Cited

U.S. PATENT DOCUMENTS

| 1,362,968 A | 12/1920 | Stewart |
| 1,606,651 A | 11/1926 | Macready |
| 1,810,827 A | 6/1931 | Hatcher et al. |
| 2,266,586 A | 12/1941 | Branum |
| 2,295,437 A | 9/1942 | Thompson |
| 2,302,996 A | 11/1942 | Lilligren |
| 2,336,539 A | 12/1943 | Gilbert |
| 2,400,046 A | 5/1946 | Hummel |
| 2,740,291 A | 4/1956 | Brown |
| 2,749,748 A | 6/1956 | Slobod et al. |
| 2,750,043 A * | 6/1956 | Thompson ............... 73/863.23 |
| 2,882,014 A | 4/1959 | Addison |
| 3,135,685 A | 6/1964 | Tanner et al. |
| 3,241,371 A | 3/1966 | Horeth |
| 3,563,255 A * | 2/1971 | Morris ....................... 209/159 |
| 3,662,897 A * | 5/1972 | Huff ............................ 210/523 |
| 4,201,082 A | 5/1980 | Dockhorn et al. |
| 4,718,289 A | 1/1988 | Barrett |
| 5,181,419 A | 1/1993 | Thompson |
| 5,372,037 A | 12/1994 | Butt |
| 5,571,962 A | 11/1996 | Georgi et al. |
| 6,386,026 B1 | 5/2002 | Zamfes |
| 6,845,657 B2 * | 1/2005 | Williams ................. 73/152.23 |
| 2005/0205118 A1 * | 9/2005 | Zamfes ..................... 134/95.2 |

FOREIGN PATENT DOCUMENTS

| CA | 814841 | 6/1969 |
| CA | 1079229 | 6/1980 |
| CA | 1280740 | 2/1991 |

* cited by examiner

*Primary Examiner*—Hezron Williams
*Assistant Examiner*—Nashmiya Fayyaz
(74) *Attorney, Agent, or Firm*—Antony C. Edwards

(57) ABSTRACT

A device for sampling drill cuttings includes a frame, an inclined perforated member mounted on the frame, a sprayer for washing cuttings down over the perforations, and a removable open-topped cuttings collector mounted under the perforated member, the perforated member cooperating with the downstream end of a vibratory screen over which the cuttings pass before translating onto the perforated screen.

16 Claims, 7 Drawing Sheets

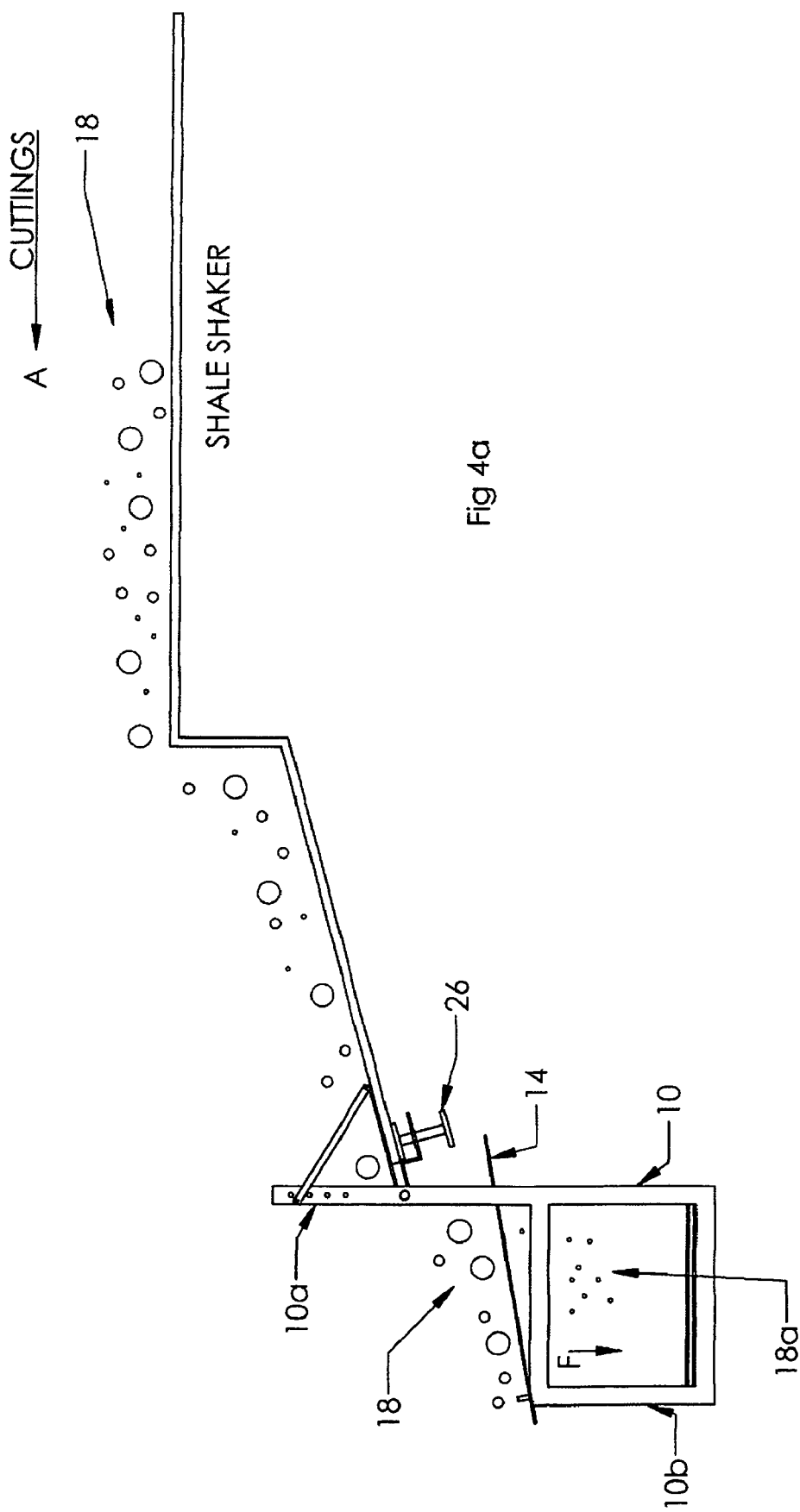

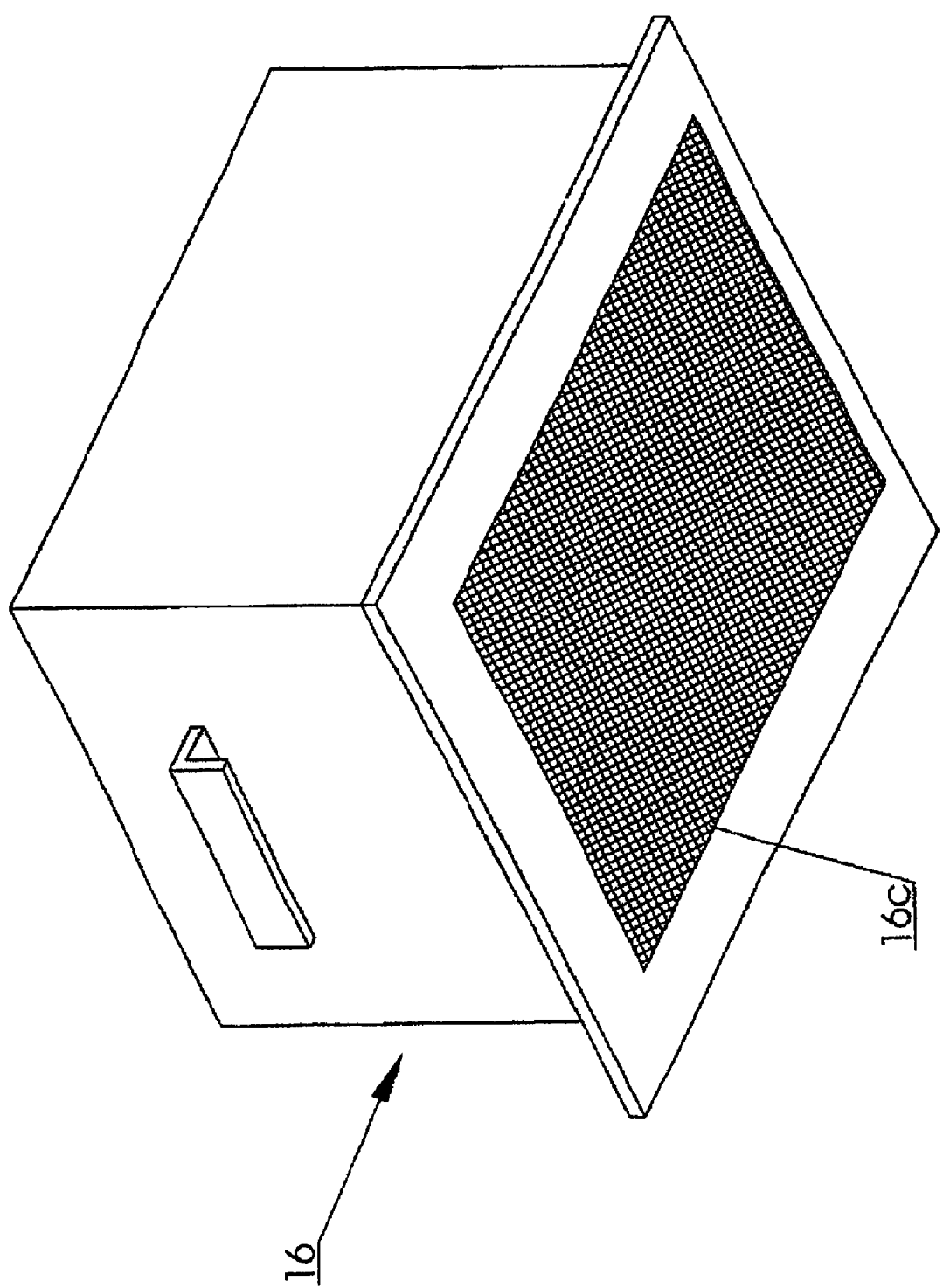

DRILL CUTTING SAMPLER

FIELD OF THE INVENTION

This invention relates to the field of methods and apparatus for taking samples from the cuttings contained in effluent including circulation fluid from a drill hole used for exploratory drilling and in particular to a sampling device mountable in cooperation with a vibratory separator used conventionally in the art for separating drill cuttings from fluid so that the fluid may be recycled for reuse.

BACKGROUND OF THE INVENTION

As stated by Barrett in his U.S. Pat. No. 4,718,289 which issued Jan. 12, 1988 for a Drill Cuttings Sample Collector, exploratory wells are drilled to evaluate penetrated rock formations for producible hydrocarbons. In drilling such wells (and in drilling production wells), circulation fluid is pumped down a string of drill pipe and through a drill bit at the lower end thereof. Such fluid thereafter circulates upwardly in the annulus between the drill pipe and the wellbore and thus flushes drill cuttings, such including drilled rock grains and fragments, from the wellbore.

In the usual operation, the drill cuttings are separated from the circulation fluid at the surface of the wellbore. The circulation fluid is thereafter recirculated through the drill string. Typically, such separation is done by a vibratory screening device; what is referred to in the industry as a shale shaker. The shale shaker comprises one or more vibrating screens. Fluid containing the drill cuttings is poured onto the screen(s) which permit the fluid to pass therethrough for recirculation. The screen(s) are inclined and vibrate the drill cuttings off one end, i.e. the lower end thereof. The drill cuttings are disposed of by burial on land or maybe put in a barge when drilling offshore.

Samples of drill cuttings which are separated from circulation fluid as described above are examined by geologists to evaluate the penetrated rock formations. Such examination is particularly important in connection with exploratory wells which are drilled for the purpose of determining the nature of the formation. It is important to collect samples from all penetrated depths so that the lithology of the formations from the surface of the well to the bottom of the bore may be accurately determined. The importance of such samples are increased when, after drilling is complete, a wireline log cannot be acquired or is of poor quality because of a damaged bore. In such cases, the cutting samples and related hydrocarbon records are the only results to show for the expense of drilling the well. It is desirable to screen out larger cuttings, which are typically referred to as cavings, and which are less likely to have been drilled during the interval of interest. Smaller sized cuttings are more likely to have been transported up the annulus at the same rate as the drilling fluid, the lag rate of which can be determined by the geologist.

As reported by Barret, in the past drill cuttings samples were collected by placing a container in the flow of drill cuttings which fell from lower end of the shale shaker. The container was periodically emptied and collected samples examined. Such prior art sample collectors suffered from several disadvantages. First, the container in which the samples accumulated would often fill to the top and overflow. Drill cuttings falling from the shale shaker when the container was full were not sampled and the record for such drill cuttings lost. This was especially true in the case of a drilling operation which was drilling at a fairly rapid rate and thus generating a high volume of drill cuttings per unit time.

Loss of drill cutting samples may also occur when fluids are accidentally introduced into the container collecting the samples. Such may occur as a result of a blinded shaker screen; i.e., the screen becomes clogged and permits circulation fluid to flow with the drill cuttings into the container. Samples may also be lost as a result of water from a hose, which is used to clean the shale shaker, entering the container. In addition, heavy rain and, in offshore drilling operations, waves may introduce water into the container, thus greatly reducing or destroying the information obtainable from the samples.

The present invention addresses the problem in the prior art where often drill cuttings are allowed to accumulate in the collector underneath the downstream end of the shale shaker, the problem being that sampling from such a collector quite often means an assistant merely scooping cuttings from the top of the collector or digging into the contents of the collector, whether or not mixed so that the actual sample taken by the assistant is not necessarily representative of the particular drilling interval which it is desired to sample.

As disclosed by Barrett in his patent referred to above, it is known to place a container under the outflow end of a so-called shale shaker, itself conventionally used in the art for removing drilling fluid from drilling cuttings. The container of Barrett is placed so as to capture drilling cuttings falling from the end of the shale shaker which as known in the art is a vibratory inclined screen conveyor which transports drill cuttings down along the inclined surface by means of vibrating the otherwise stationary surface of the screen whilst allowing circulation fluid to pass through the vibratory surface for collection and reuse. What Barrett fails to disclose, and which is one object of the present invention to provide, is an improved method and apparatus for screening, filtering or culling a selectively smaller volume of the drill cuttings exiting the shale shaker so that the sample still represents a uniform sampling of the desired drilling cross-section exhibited by the drilling cuttings exiting the shale shaker.

Other prior art of which applicant is aware include:

Canadian Patent No. 1,280,740 which issued to Hoeft on Feb. 26, 1991 for a Chip Sampler. Canadian Patent No. 1,079,229 which issued to Huff on Jun. 10, 1980 for a Mud Metering Testing and Cleansing System. Canadian Patent No. 814841 which issued to Morris on Jun. 10, 1969 for An Apparatus for Collecting and Washing Well Cuttings. U.S. Pat. No. 5,571,962 which issued to Georgi on Nov. 5, 1996 for a Method and Apparatus for Analyzing Drill Cuttings. U.S. Pat. No. 5,372,037 which issued to Butt on Dec. 13, 1994 for Soil Sampling Apparatus. U.S. Pat. No. 3,135,685 which issued to Tanner on Jun. 2, 1964 for a Device for Collecting Cutting Samples From Well Drilling Operations. U.S. Pat. No. 2,336,539 which issued to Gilbert on. Dec. 14, 1943 for a Sampling Device.

SUMMARY OF THE INVENTION

In summary, the present invention may be characterized in one aspect as a device for sampling drill cuttings which includes a frame, an inclined perforated member, a sprayer, and a removable cuttings collector. The frame is mountable to, so as to cooperate with, a downstream end of a vibratory screen over which drill cuttings are passed in a downstream flow direction so that vibratory motion of the vibrating screen is transmitted at least in part to the frame. The inclined perforated member, preferably a planar member, is mounted on the frame, the planar member including a plate or sieve screen having perforations over at least a portion thereof between an upstream end and a downstream end of the planar member.

The perforations are sized to screen out those cuttings exceeding a predetermined size and to allow to pass through the perforations those cuttings equal to or less than the predetermined size. The perforations are disposed on the planar member so that a substantially linear flow path between the upstream and downstream ends of the planar member along which cuttings translate pass over so as to intersect a plurality of the perforations. The sprayer is mounted adjacent the upstream end of the planar member so as to direct fluid spray downstream along the planar member and over the perforations.

The open-topped cuttings collector is removably mounted in the frame so as to be insertable into the frame into a collecting position disposed beneath the perforations on the perforated planer member, and removable from the frame so that the cuttings may be removed from the collector for analysis.

The upstream end of the planar member has an inlet width which is less than a corresponding width of the downstream end of the vibratory screen so that only a pre-selected ratio of the cuttings on the vibratory screen are entrained onto the upstream end of the planar member. The drill cuttings for any particular drill-hole cross-section may thus be uniformly sampled and the resulting sample of a selectively pre-determined volume for ease of and efficient removal for analysis.

In one embodiment the collector is a perforated container for straining fluid from the cuttings passing into the collector through the perforations in the planar member. The collector may be a rigid walled container having a base comprising a mesh screen. The mesh screen of the base of the collector may have a sieve screen mesh size which allows fluids and any particles smaller than the sieve screen mesh size to pass through the mesh screen, while retaining on the mesh screen cleaned cuttings larger than the sieve screen mesh size. The planar member may include a sieve screen having uniformly sized mesh.

The planar member may be a plate, and the plate may be inclined in the range of substantially 10-30 degrees from the horizontal so as to elevate the upstream end of the planar member to cooperate with the downstream end of the vibratory screen when the frame is mounted adjacent the downstream end of the vibrating screen so that the cuttings translating in the flow direction flow from the vibrating screen onto the plate. The plate is inclined so that cuttings travel from the upstream end to the downstream end and subsequently off the downstream end. In one embodiment the planar member is inclined substantially 15 degrees from the horizontal.

The frame may define a drawer support and the collector may be a perforated drawer for draining fluid from the cuttings while retaining the cuttings in the drawer. The drawer may be selectively drawn out from under the planar member and selectively slid back into the frame so as to align an open top of the drawer under the perforations on the planar member. The collector may be a first collector and removable from the frame so that a second, empty collector may be inserted into the frame in place of the first collector once the first collector has accumulated a sample of the drill cuttings passing through the perforations in the planar member. The drawer may be entirely removable from the frame.

In one embodiment the perforations on the planar member are of non-uniform diameter. In particular, the perforations on the planar member may include first and second apertures having two different first and second aperture diameters respectively. The perforations in the planar member may be formed as adjacent arrays of apertures. The apertures in a single array may have alternating first and second aperture diameters. A plurality of adjacent single arrays may be offset relative to one another so that along the flow path, the flow path intersects apertures having both the first and second aperture diameters.

BRIEF DESCRIPTION OF THE DRAWINGS

FIG. 4a is, in side elevation view, an alternative embodiment of the cutting samples according to the present invention.

FIG. 4b is an enlarged view of the view of FIG. 4a.

FIG. 5 is, in bottom perspective view, the removable cutting collector of the cutting sampler of FIG. 1.

DETAILED DESCRIPTION OF EMBODIMENTS OF THE INVENTION

Figure 1:
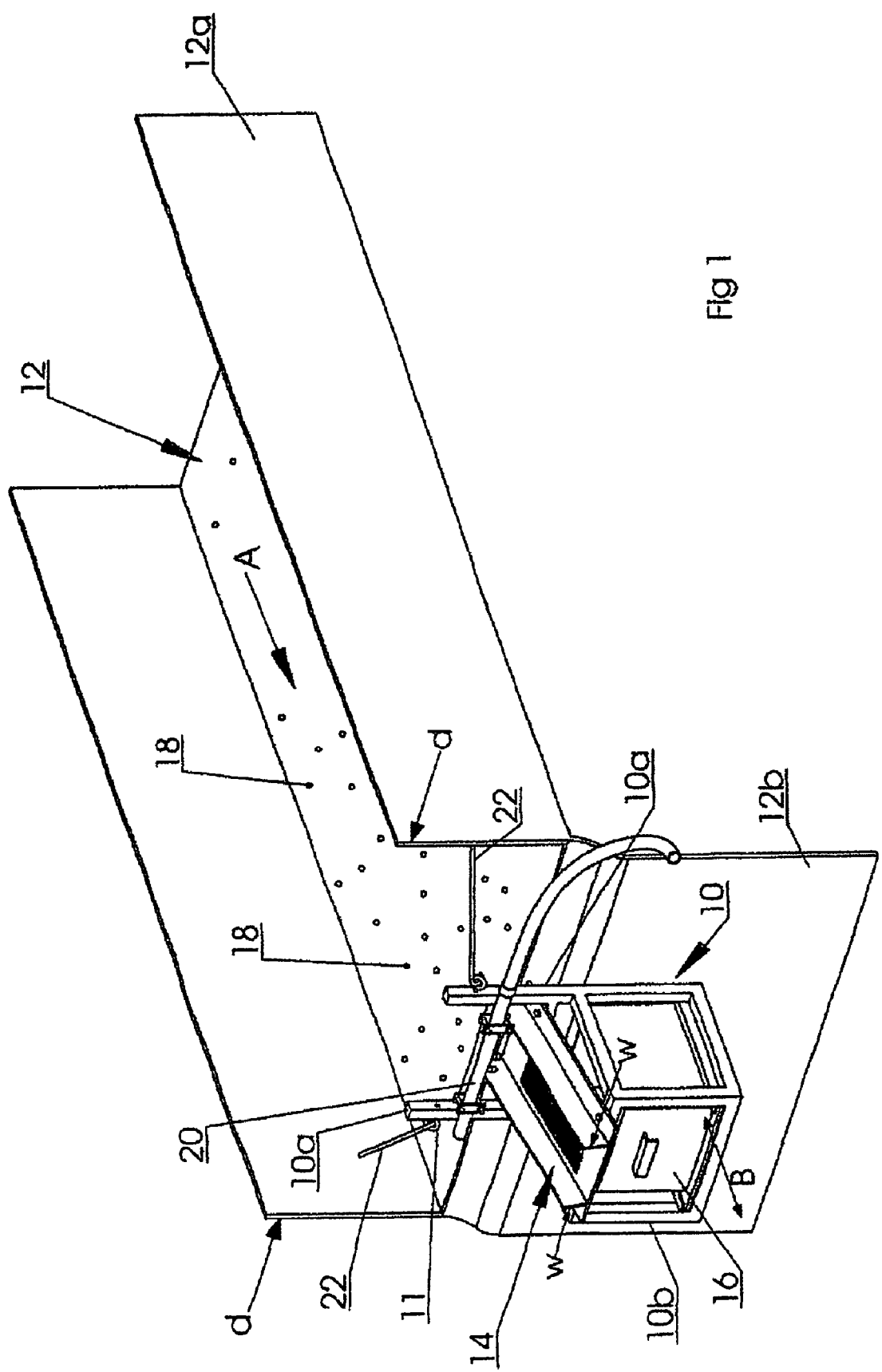
FIG. 1 is, in perspective view, a cutting sampler according to one embodiment of the present invention mounted at the downstream end of a shale shaker.
Figure 2:
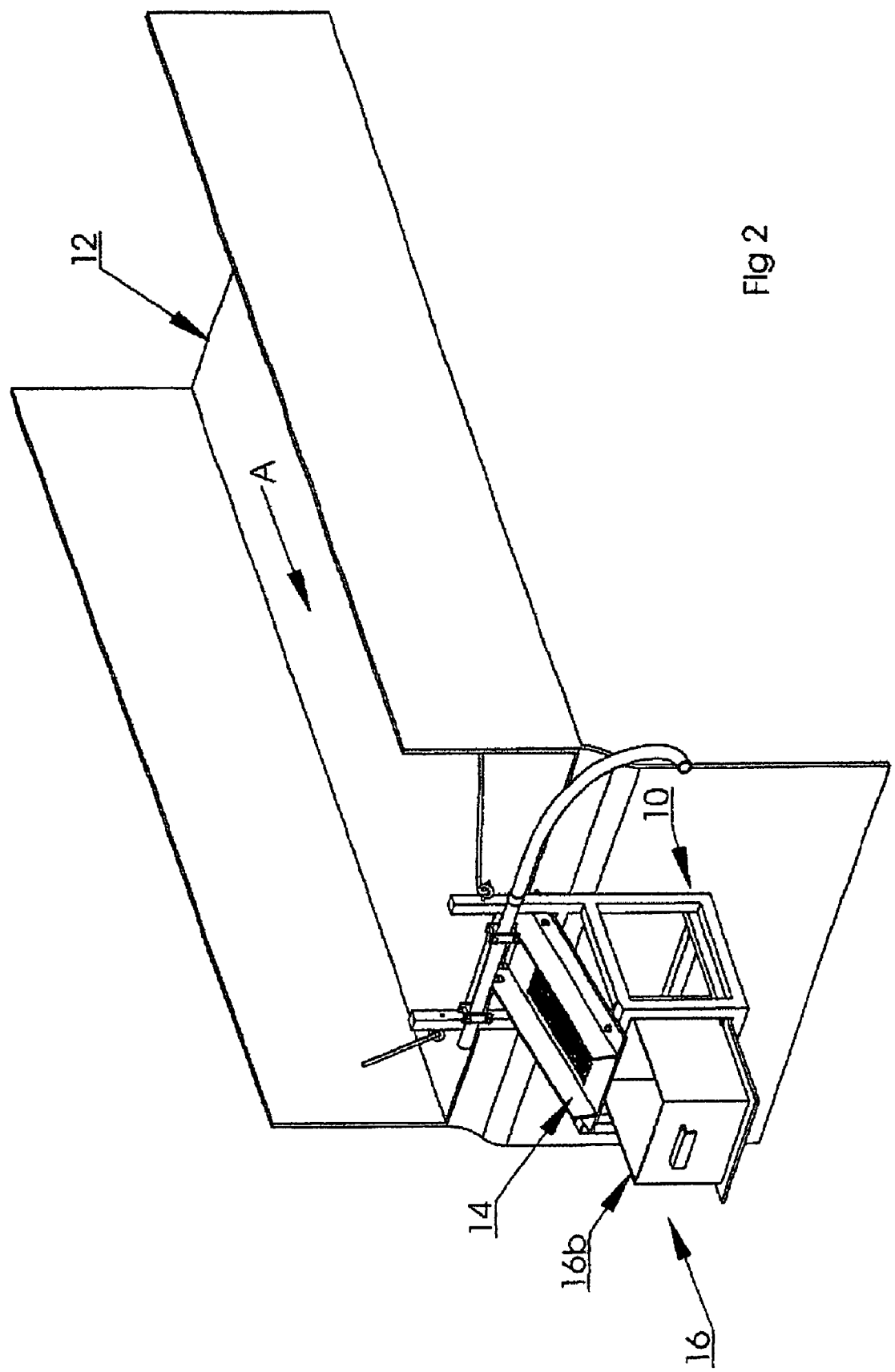
FIG. 2 is the view of FIG. 1 with the removable cutting collector which forms part of the cutting sampler according to the present invention partially removed.

As may be seen in the accompanying figures wherein like characters of reference denote corresponding parts in each view, the drill cutting sampler according to one embodiment of the present invention includes a supporting frame 10 adapted to be mounted in cooperation with the downstream end of a shale shaker 12 for supporting a perforated plate or sieve screen (also collectively herein referred to as perforated plate 14) in the outflow path of drill cuttings exiting the shale shaker, the perforated plate or sieve screen cooperating with a removable cutting collector 16 removably mounted beneath the perforated plate or sieve screen for collecting a sampling of cuttings passing over perforated plate 14 wherein a percentage of the cuttings 18 are washed by spray water from a sprayer 20 through perforations 14a of perforated plate 14. Perforated plate 14 allows cuttings of a desired size to pass through into the collector 16 while all undesired larger cuttings are rejected and pass over the plate, being both washed away and vibrated off. That is, the sample washer according to the present invention, and in particular plate 14 is mounted so as to utilize the vibration from the shale shaker in order to aid in separation of the desired size of particle. The desired size or sizes of particle fall through the apertures or perforations 14a in perforated plate 14 so as to fall into collector 16. Thus the desired size or sizes of particles are separated from larger sized, undesired cuttings which are vibrated and washed off the lower end of perforated plate 14.

Thus drill cuttings 18 on the shale shaker translate downwardly along the downwardly inclined vibrating screen of the shale shaker in direction A so as to exit from The downstream-most end of the shale shaker.

Supporting frame 10 may be held in place at the downstream end of shale shaker 12 by any conventional means that supports it in place. The frame includes a vertically disposed pair of parallel, laterally spaced apart uprights 10a. The uprights 10a may be clamped directly to the shale shaker or held in place by ties or struts 22 which are rigidly mounted at one end to, for example, some part of the rigid supporting structure 12a of shale shaker 12 and at their other ends rigidly to the upper ends of uprights 10a. For example, struts 22 may be mounted to uprights 10a by means of I-bolts 11. The lower end of supporting frame 10 may be free hanging or attached to some other rigid part 12b, for example, on the downstream end of shale shaker 12.

A generally cubic framework 10b is rigidly mounted to vertical uprights 10a so as to extend cantilevered therefrom. Frame 10b supports a pair of rails 24 in opposed facing relation mounted in the bottom of frame 10b. The base flanges 16a extending laterally outwardly from the base of collector 16 are slidably mounted within rails 24 so that collector 16 may be slid in direction B into and out of frame 10b. Collector 16 may thus be easily removed from, and replaced back into, frame 10b The uppermost end of perforated plate 14 is mounted adjacent that is, so as to be in the flow path of cuttings leaving the downstream-most end of shale shaker 12 so that drill cuttings 18 vibrating downwardly in direction A along the downward incline of shale shaker 12, will, if aligned with the opening between, side walls 14b, fall onto or otherwise transfer onto the upstream-most end of perforated plate 14. Sprayer 20 sprays fluid such as water from nozzles 20a, for example in a spray pattern C, to thereby flush cuttings 18 in direction D to urge the cuttings over the perforations 14a. The spray cleans the cuttings and those which are of desired size fall into the collector, and also flushes undesired cuttings off perforated plate 14. The spray also washes away any remnant drilling fluid which was not separated from cuttings by the shale shaker, resulting in a much cleaner sample. The remainder of the cuttings 18 exiting the downstream end of shale shaker 12, if they fall outside of the spacing between walls 14b, merely fall as waste from the shale shaker and are disposed of conventionally. Consequently, the percentage of cuttings transported along shale shaker 12 which are to be sampled may be initially governed by the width between walls 14b, that is, the ratio of the width w to the overall width d of the downstream outflow end of shale shaker 12. As may be seen in the representation of perforations 14a in FIG. 3a, in the example where width w is six inches, the upstream end of perforated plate 14 may have an un-perforated infeed area under spray nozzles 20a which may be approximately three inches long measured in the direction of flow, and may have an un-perforated area at the downstream-most end of approximately two inches. These dimensions may advantageously correspond to the position of the open-topped removable collector 16 mounted in frame 10b, that is, positioned so that the open top of collector 16 is mounted vertically under the perforations 14a. Perforated plate 14 may also be a sieve screen of a standard mesh size (that is 10 mesh, 20 mesh, etc). Such a sieve screen would thus have all perforations the same size.

Figure 4B:
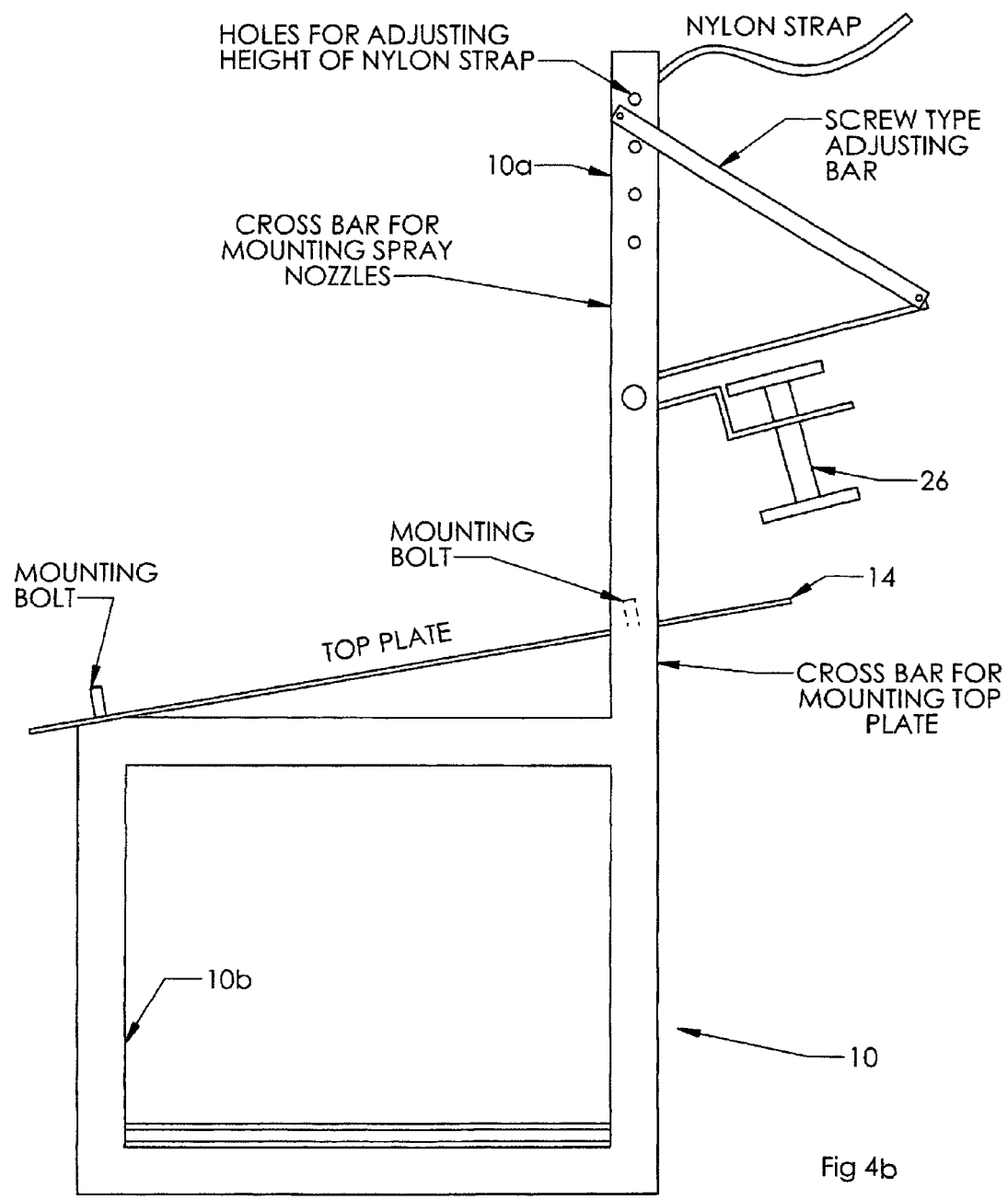

As seen in the alternative embodiment of FIGS. 4a and 4b, which are not intended to be limiting, perforated plate 14 is not necessarily directly connected to the shaker. When uprights 10a are attached to shaker 12 using clamps 26, perforated plate 14 hangs just below the downstream end of shaker 12 in the path of cuttings falling from the shaker.

Figure 3:
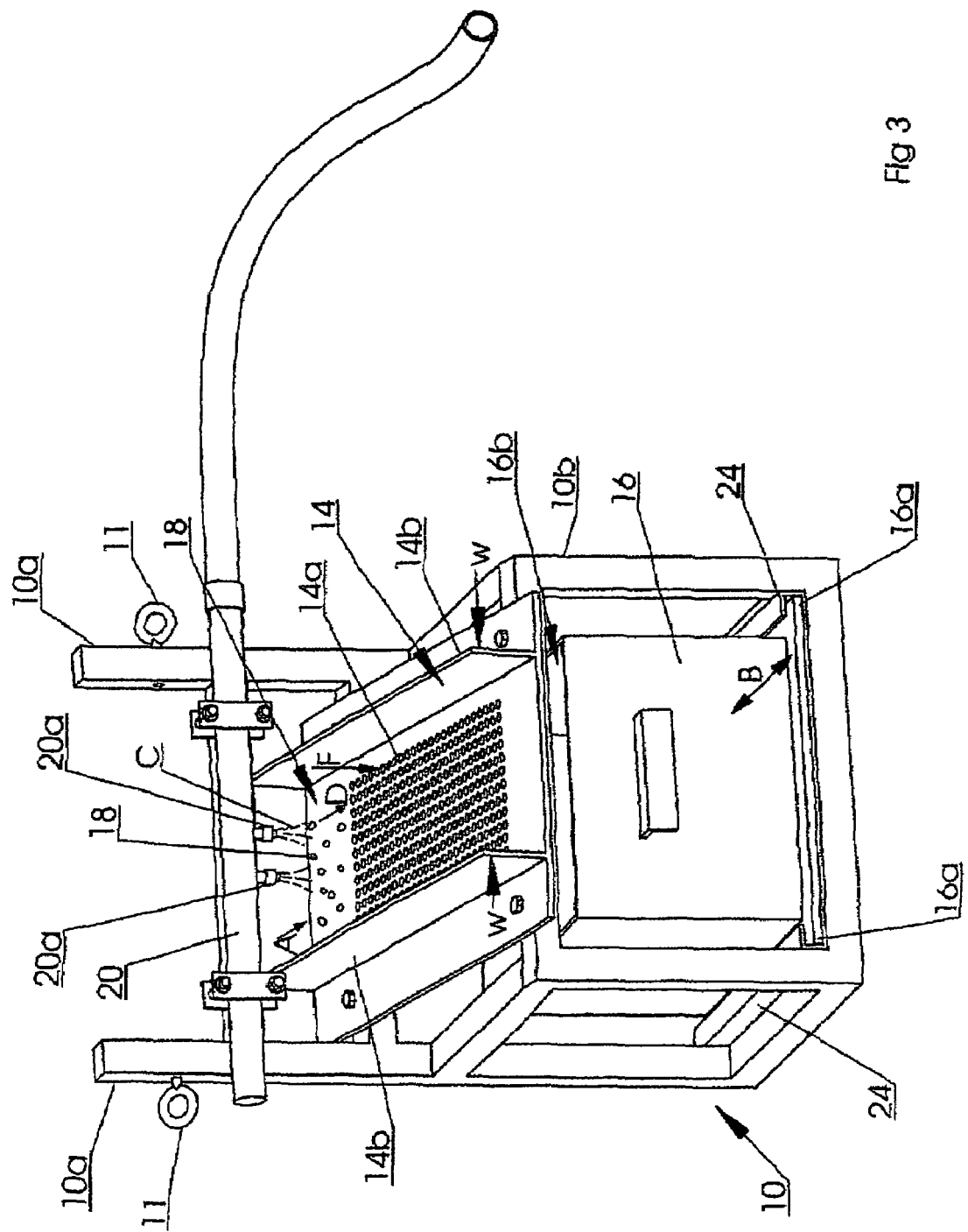
FIG. 3 is, in perspective view, the cutting sampler of FIG. 1.
Figure 3A:
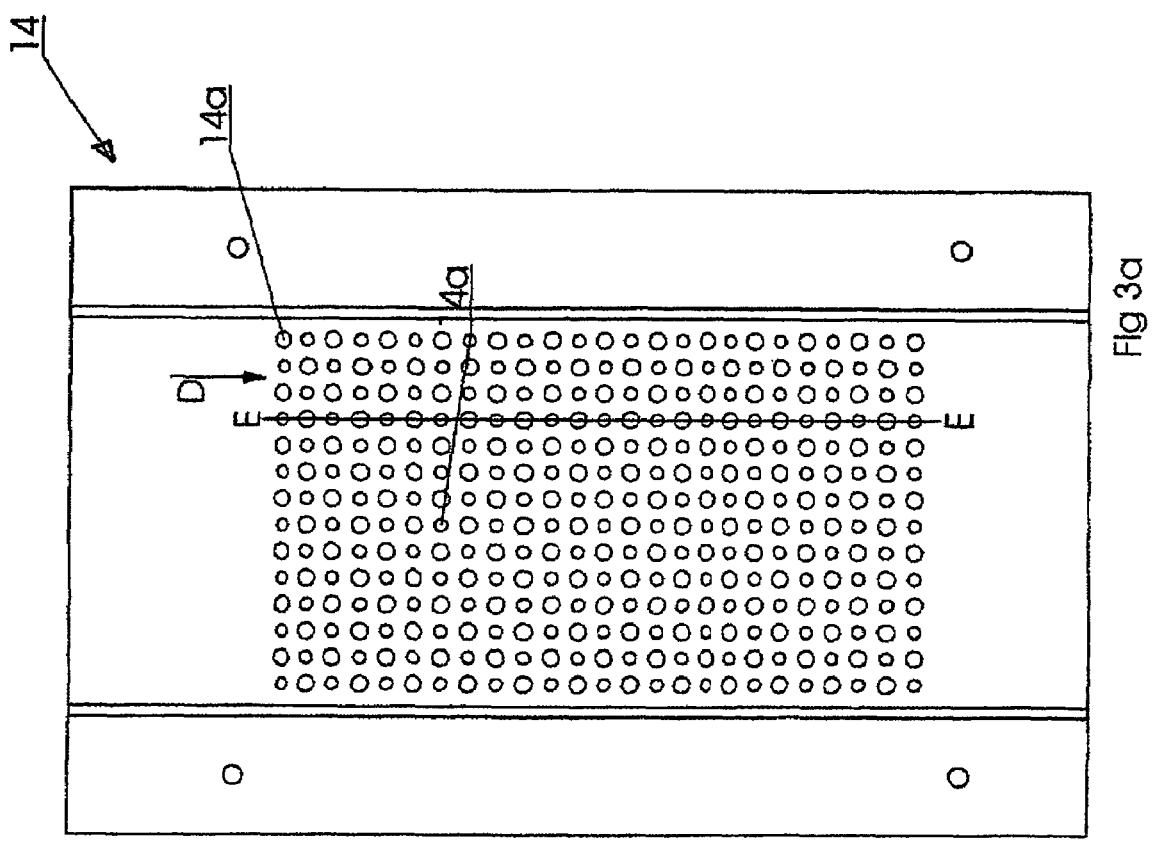
FIG. 3a is, in plan view, the perforated plate of the cutting sampler of FIG. 3.

As may also be seen in FIG. 3a, perforations 14a may or may not be of uniform size and in one particular preferred embodiment, not intended to be limiting, may consist of arrays of apertures which may alternatingly be of one quarter inch diameter and three sixteenth inch diameter. The arrays of apertures may be laterally disposed linear arrays in which alternating laterally disposed rows of apertures are offset from each other so that along any given linear downstream flow path over the apertures, for example along flow path E, cuttings moving along flow path E in direction D are flushed by spray from nozzles 20a over alternatingly sized apertures. In the example given, cuttings 18 flowing on path E flow over apertures which alternate between one quarter inch diameter and three sixteenth inch diameter. Cuttings 18 flowing in direction D urged by the fluid spray from nozzles 20a, and assisted by vibration from shale shaker and the inclination of plate 14,are thus flushed over, and a percentage of cuttings 18 of desired size thus flushed through, apertures 14a in direction F so as to fall into collector 16 through the upper opening 16b of the collector.

The flow rate of cuttings 18 passing over apertures 14a for example is governed by the pressure and volume of spray from nozzles 20a, and the vibration from shaker 12 and the inclination from the horizontal of perforated plate 14. These factors as well as the aperture size of perforations 14a, that is, in the case of sieve screens including the mesh size of the sieve screen govern the volume and rate at which cuttings 18 pass through perforations 14a in direction F and thus the sample rate of, and the volume of, the sampling 18a of cuttings 18. In the illustrated embodiment, advantageously, perforated plate 14 may be inclined in the range of 10-30 degrees from the horizontal, and in particular may be inclined approximately 15 degrees.

Thus, after a pre-determined drilling interval has been accomplished, for example every five meters, the corresponding sample 18a of desired size of drill cuttings 18 may be collected for storage and later analysis, by removing collector 16 from underneath perforated plate 14 and by inserting a second empty collector 16 so as to commence collecting samples from the next drilling interval. As may be seen in FIG. 5, advantageously, the base 16c of collector 16 may be a fine screen or mesh, for example, 120 mesh screen supported by, for example, a metal support grate (not shown). Mesh screen allows the fluid from nozzles 20a to drain from collector 16 leaving only washed cuttings 18.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A device for sampling drill cuttings comprising:
  a frame directly mountable to and supported by, so as to cooperate with, a downstream end of a vibratory screen over which drill cuttings are passed in a downstream flow direction so that vibratory motion of the vibrating screen is transmitted at least in part to said frame,
  an inclined perforated planar member mounted on said frame, said planar member including a plate or sieve screen having perforations over at least a portion thereof between an upstream end and a downstream end of said planar member wherein said perforations are sized to screen out those cuttings exceeding a pre-determined size and to allow to pass through said perforations those cuttings equal to or less than said pre-determined size, and wherein said perforations are disposed on said planar member so that a substantially linear flow path between said upstream and downstream ends of said planar member along which cuttings translate pass over so as to intersect a plurality of said perforations, a sprayer mounted adjacent said upstream end of said planar member so as to direct fluid spray downstream along said planar member and over said perforations, an open-topped cuttings collector removably mounted to said frame so as to be insertable into a collecting position disposed beneath said perforations on said perforated planar member, and removable from said frame so that the cuttings may be removed from said collector for analysis, wherein said upstream end of said planar member has an inlet width which is less than a corresponding width of the downstream end of the vibratory screen so that only a pre-selected ratio of the cuttings on the vibratory screen are entrained onto said upstream end of said planar member, whereby, the drill cuttings for any particular drill-hole cross-section are uniformly sampled and the resulting sample of a selectively pre-determined volume for ease of and efficient removal for analysis.

2. The device of claim 1 wherein said collector is a perforated container for straining fluid from the cuttings passing into said collector through said perforations in said planar member.

3. The device of claim 2 wherein said collector is a rigid walled container having a base comprising a mesh screen.

4. The device of claim 1 wherein said planar member is a plate, and wherein said plate is inclined in the range of substantially 10-30 degrees from the horizontal so as to elevate said upstream end of said planar member to cooperate with the downstream end of the vibratory screen when said frame is mounted adjacent the downstream end of the vibrating screen so that the cuttings translating in the flow direction flow from the vibrating screen onto said plate, and wherein said plate is inclined so that cuttings travel from said upstream end to said downstream end and subsequently off said downstream end.

5. The device of claim 4 wherein said planar member is inclined substantially 15 degrees.

6. The device of claim 1 wherein said frame defines a drawer support and wherein said collector is a perforated drawer for draining fluid from the cuttings while retaining the cuttings in the drawer, and wherein said drawer is selectively drawn out from under said planar member and selectively slid back into said frame so as to align an open top of said drawer under said perforations on said planar member.

7. The device of claim 1 wherein said collector is a first collector and removable from said frame so that a second, empty collector maybe inserted into said frame in place of said first collector once said first collector has accumulated a sample of the drill cuttings passing through said perforations in said planar member.

8. The device of claim 6 wherein said drawer is entirely removable from said frame.

9. The device of claim 1 wherein said perforations on said planar member are of non-uniform diameter.

10. The device of claim 9 wherein said perforations on said planar member include first and second apertures having two different first and second aperture diameters respectively.

11. The device of claim 9 wherein said perforations in said planar member are formed as adjacent arrays of apertures.

12. The device of claim 11 wherein said apertures include apertures having different, first and second aperture diameters, and wherein, in a single array of said arrays of apertures, said apertures in said single array having alternating said first and second aperture diameters.

13. The device of claim 12 wherein a plurality of adjacent said single arrays are offset relative to one another so that along said flow path, said flow path intersects apertures having both said first and second aperture diameters.

14. The device of claim 3 wherein said mesh screen of said base of said collector has a sieve screen mesh size which allows fluids and any particles smaller than said sieve screen mesh size to pass through said mesh screen, while retaining on said mesh screen cleaned cuttings larger than said sieve screen mesh size.

15. The device of claim 1 wherein said perforations on said planar member are of uniform diameter.

16. The device of claim 15 wherein said planar member includes a sieve screen having uniformly sized mesh.

* * * * *